United States Patent [19]

Dirr, Jr.

[11] Patent Number: 5,267,978

[45] Date of Patent: Dec. 7, 1993

[54] PULSED DROP DETECTOR FOR INTRAVENOUS SYSTEMS

[75] Inventor: William J. Dirr, Jr., Cincinnati, Ohio

[73] Assignee: Random Corporation, Cincinnati, Ohio

[21] Appl. No.: 575,400

[22] Filed: Aug. 29, 1990

[51] Int. Cl.$^5$ ............................................. A61M 5/00
[52] U.S. Cl. ......................... 604/246; 128/DIG. 13; 604/253
[58] Field of Search ...................... 604/65, 67, 66, 251, 604/253, 246; 346/1.1; 364/551.61, 571.61; 128/662.01; 250/207; 328/117; 73/861.78, 861.18, 861.23

[56] References Cited

U.S. PATENT DOCUMENTS

| | | | |
|---|---|---|---|
| 3,714,441 | 1/1973 | Kreda | 250/207 |
| 3,762,221 | 10/1973 | Coulthard | 128/662.01 |
| 3,845,400 | 10/1974 | Yee | 328/117 |
| 4,404,860 | 9/1983 | Wood et al. | 73/861.78 |
| 4,498,901 | 2/1985 | Finch | 604/253 |

Primary Examiner—C. Fred Rosenbaum
Assistant Examiner—Manuel Mendez
Attorney, Agent, or Firm—Eugene F. Friedman

[57] ABSTRACT

A drop detector for intravenous systems in which an infrared emitter is pulsed at 10 kHz. The pulsed radiation passes through a drip chamber and then to a detector. The detector circuit determines the amplitude modulation of the 10 kHz. carrier frequency. This provides an indication of when the drop falling through the drip chamber has interrupted the light beam. An automatic gain control circuit maintains the output of the detector, on a long time constant basis, at a constant level to eliminate the vagaries of drip chambers with different optical characteristics and the like. When the AGC circuit lacks the ability to maintain the output of the detector circuitry at a constant level, a fault detector provides an alarm to indicate that the circuitry has exceeded its operational range.

17 Claims, 3 Drawing Sheets

PULSED DROP DETECTOR FOR INTRAVENOUS SYSTEMS

REFERENCE TO RELATED APPLICATION

The present application may find use in particular with the optical and mechanical arrangements shown in U.S. patent application Ser. No. 7/575,401 of William J. Dirr, Jr. and Thomas E. Kimble filed on Aug. 29, 1990.

BACKGROUND

The systems for administering intervenous fluids to patients now generally include a control circuitry to assure the delivery of the proper amount of liquid. To make this determination, the control system often includes some manner of ascertaining the actual amount of fluid received by the patient. Generally, to make this determination, the control system will include a drop detector to actually count the number of drops of fluid flowing from the bottle of I.V. solution. The rate of drops passing through a drip chamber effectively provides knowledge as to the amount of solution passing into the patient.

The determination that a drop has indeed fallen through the drip chamber generally involves the passage of a beam of electromagnetic (em.) radiation through the chamber. The passage of the drop disturbs the beam of radiation which the control circuitry then attempts to determine.

However, control circuits utilizing radiation to determine the passage of a drops suffers from the ubitiquous presence of radiation of almost all wavelengths in the area of the drip chamber. Virtually any source of light will interfere with the determination of the number of drops.

Thus, such control systems generally make extensive efforts to shield the drip chamber from any source of ambient light. This entails additional expense to place the drip chamber in substantially total darkness (aside from the radiation used to determine a drop).

However, a drop passing through the beam of radiation often does not effectuate a major disturbance of that beam. Thus, even minimal amounts of ambient light can seriously interfere with the proper determination. Moreover, should an attendant attempt to make sure that the fluid flows from the bottle to the patient, opening the door of the device can add so much light as to seriously disrupt the determination. At night, the attendant may have to use a flashlight to make the visual determination. In a darkened room, the light from such a source will, even under the most desirable circumstances, often create a false reading.

Accordingly, the search continues for a system that will result in the reliable determination of the amount of I.V. fluid flowing to a patient. The system should generally display very little, if any, suseptibility to disruption by ambient light.

SUMMARY

Pulsing the source of radiation at a high frequency compared to the length of time required for the drop to fall through the beam and determining the amplitude modulation of the received pulse beam will reduce and often eliminate many of the problems encountered with prior drop detectors. A drop detector employing pulsed electromagnetic radiation includes first an emitter means which provides an output of em. radiation of a generally specified wave length. A pulsing mean couples to the emitter means. It pulses on and off at a particular frequency the output of the emitter means.

A receiver means has a location in a position to receive the em. radiation from the emitter means. Upon the receipt of this em. radiation, it provides a characteristic signal.

A detector means couples to the receiver means. It has the function of detecting the amplitude modulation of the component of the electrical signal provided by the receiver means having the particular frequency at which the pulsing means pulses the output of the emitter means. This amplitude modulation results from and thus provides an indication of the passage of a drop in the area between the emitter means and the receiver means.

The method of detecting drops moving through an area involves first passing through that area a beam of em. radiation with a specified wave length and pulsed at a particular frequency. At least a portion of this beam, after it has passed through the area, is received. Lastly, detecting the amplitude modulation of the component of the beam having the particular pulsed frequency will permit the determination of the passage of a drop through the area.

DETAILED DESCRIPTION

Figure 1:
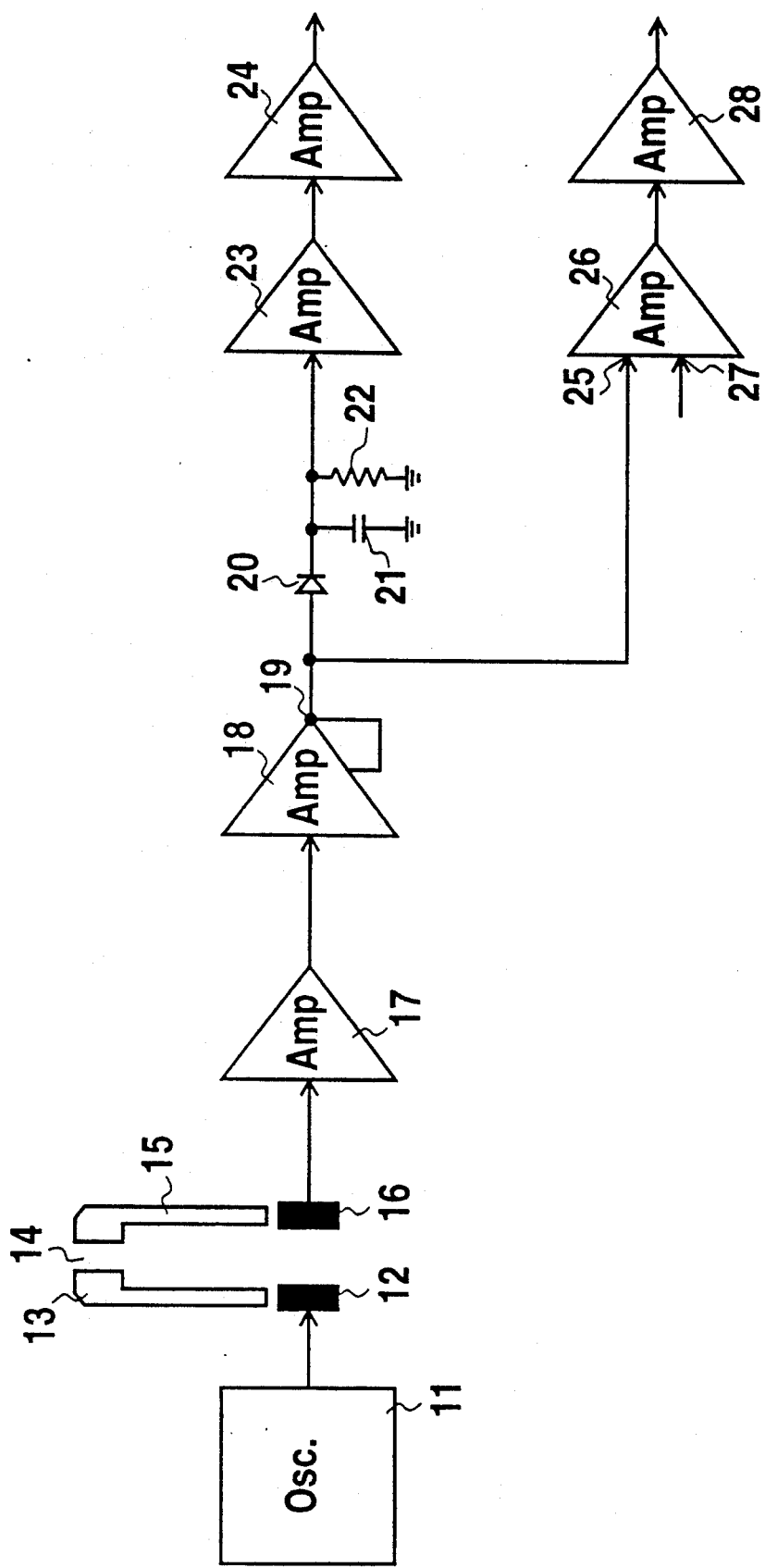
FIG. 1 provides a block diagram of an electronic circuit creating and utilizing pulsed em. radiation to detect falling drops.

In the circuit shown in FIG. 1, the oscillator 11 produces at the IR emitter 12 infrared radiation pulsed on and off at 10 kHz. The optics 13 transmit this IR radiation into the area 14 where the drip chamber sits. After traversing the drip chamber in the area 14, the radiation passes through the optics 15 which transmits it to the IR detector 16. The electrical signal produced by the IR detector then passes to the band pass filter 17 indicated diagrammatically in the figure as an operational amplifier. The filter 17 centers upon the pulse frequency of 10 kHz. From the band pass filter 17, the signal travels to the automatic gain control circuit 18 which, on a long time basis, maintains a substantially constant signal at its output 19.

The diode 20, capacitor 21, and resistor 22 measure the amplitude modulation of the signal leaving the output 19 of the automatic gain control circuit 18. The amplitude modulation signal, stripped thus of its carrier frequency, undergoes amplification at the amplifier 23 and then passes to the analog to digital conversion at the converter 24. Its signal thus provides a measure of whether a drop has passed through the area 14 between the emitter optics 13 and the receiver optics 15.

The output of the AGC circuit 18 also passes to the upper input 25 of the comparator 26. The comparator 26 provides an output when the signal at its upper input 25 falls below the reference signal as its lower input 27. This indicates that the automatic gain control 18 cannot maintain its output at a predetermined level and that some fault has appeared in the circuit. The fault detector signal then passes to the analog to digital converter 28 which modifies the signal for further treatment.

Figure 2A:
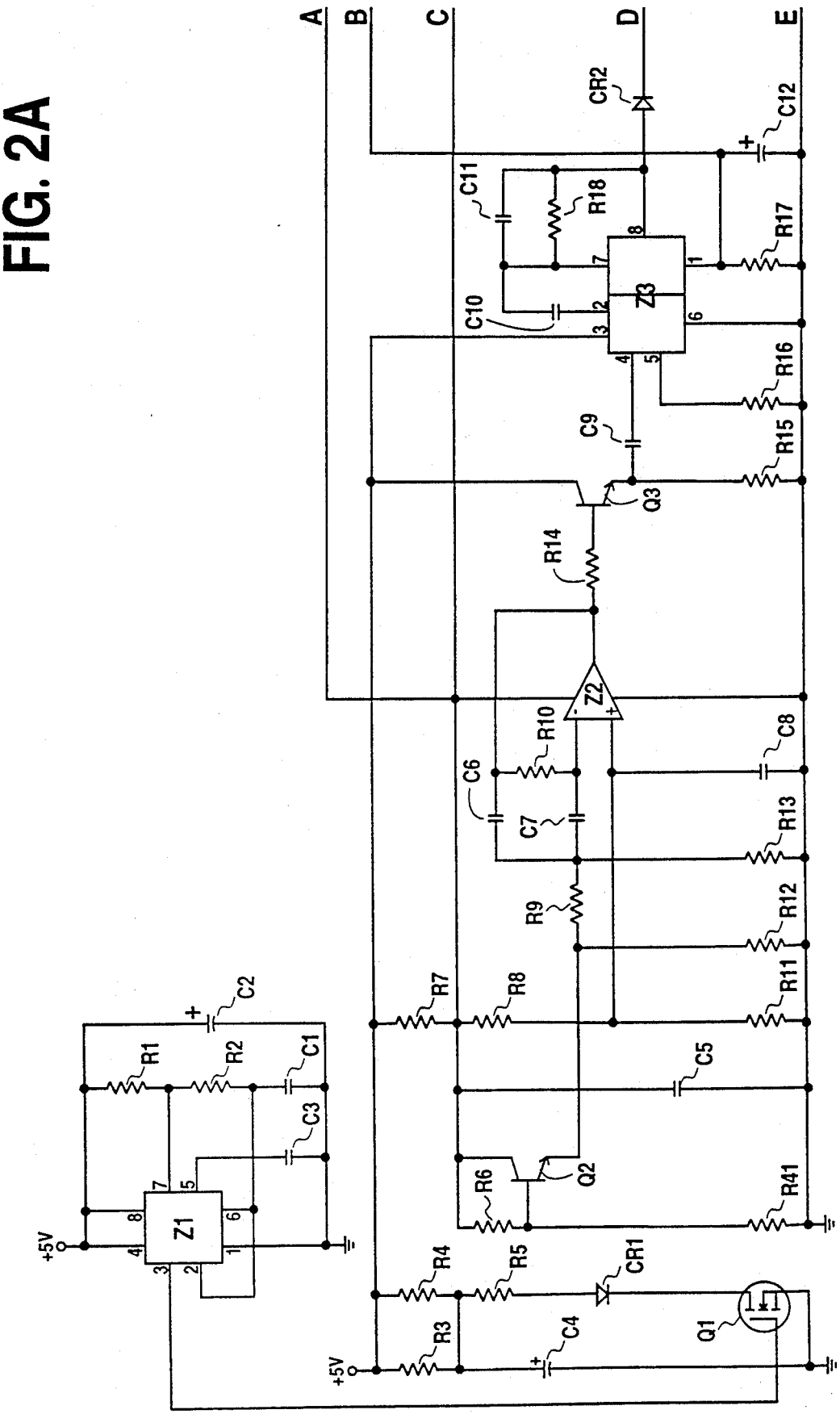
FIGS. 2A and 2B give, respectively, the left and right halves of an actual circuit constructed according to the block diagram of FIG. 1. The figures connect along the leads A through E shown on the right side of FIG. 2A and on the left side of FIG. 2B.
Figure 2B:
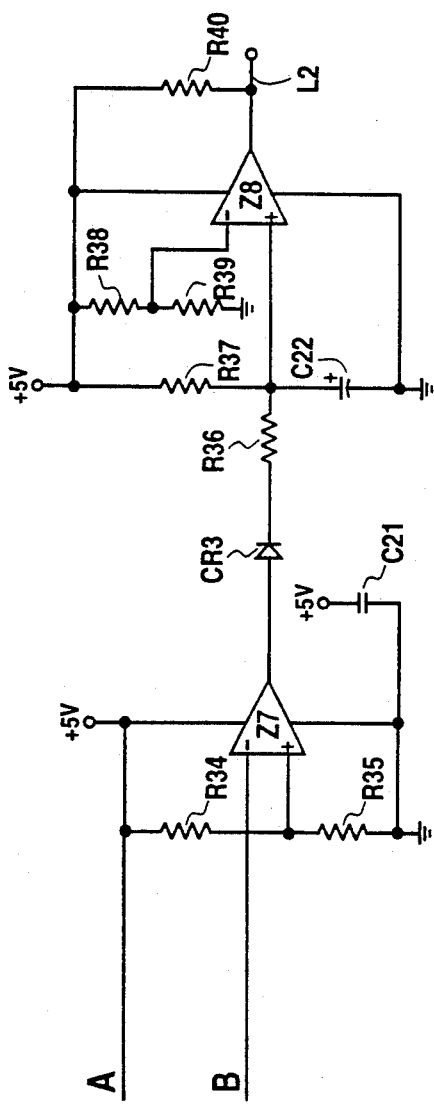
Figure 2B:
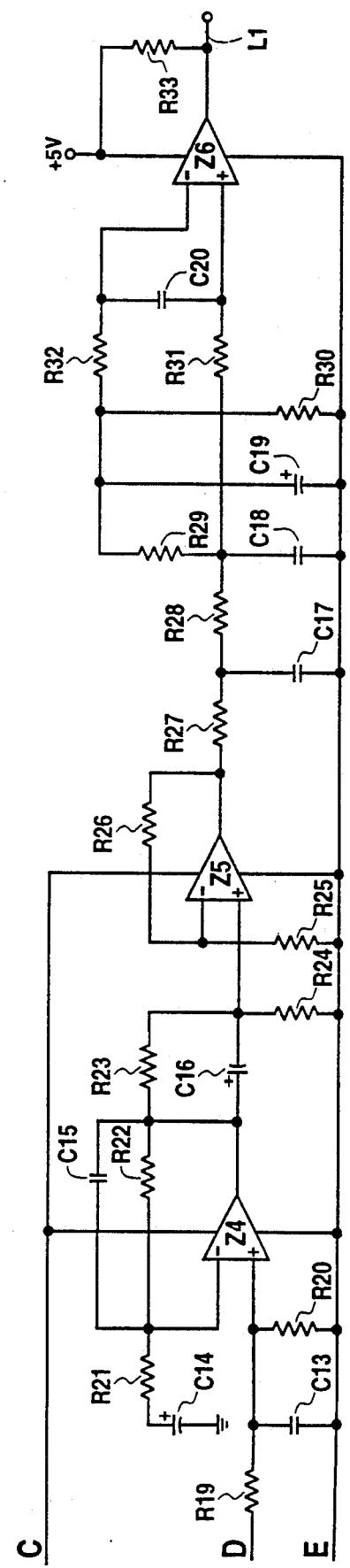

Comparing the circuit of FIG. 1 with that of FIGS. 2A and 2B, the oscillator 11 includes the timer Z1 which has its frequency determined by the resistors R1 and R2 and the capacitor C1. The capacitor C2 filters the 10 kHz. signal which then appears at the base of the field effect transistor Q1 to pulse it on and off at the stated frequency. The pulsed current, passing through the light emitting diode CR1, provides infrared radiation, also pulsed at 10 kHz. This light, passing through the emitter optical path, the drip chamber, and the receiver optical path, strikes the photosensitive transistor Q2. The band pass filter 17 then includes the operational amplifier Z2, the resistors R6 to R13 and the capacitors C5 through C8. The automatic gain control circuit 18 includes first the emitter follower composed of the transister Q3, the resistors R14 and R15, and the capacitor C9. This provides a buffer between the high impedence output of the band pass filter's amplifier Z2 and the low impedence input of the preamplifier Z3, the left hand portion of which also forms part of the emitter follower circuit. The remainder of the automatic gain control includes the other half of the preamplifier Z3, the resistors R16 to R18 and the capacitors C10 through C12. The amplitude modulation detector 20-22 includes the diode CR2 which acts as a rectifier and the resistors R19 and R20 and the capacitor C13. The last three components act as a low-pass filter.

The automatic gain control circuit 18 maintains its output at a constant level regardless of the applicable characteristics of the drip chamber placed between the emitter 12 and the receiver 16 or other factors. If the output of the automatic gain control circuit, specifically that of the preamp Z1, falls below its predetermined level, then the voltage across the resistor R17 and the capacitor C12 declines which will provide a fault alarm as discussed below. This would indicate that the circuit is not operating properly.

The first stage of the amplifier 23 includes the op. amp. Z4 along with its associated resistors R1 to R24 and capacitors C14 to C16. The second stage of amplification includes the op. amp. Z5 with its associated resistors R25 to R27 and its capacitor C17.

The analog to digital converter for the drop detector itself centers on the op. amp. Z6. The support for its functioning include the resistors R28 to R33 and the capacitors C18 to C20. Its output appears along the lead L1.

As indicated above, the preamp. Z3 attempts to maintain its output 8 at a constant level. If it fails to do so, then the voltage across the resistor R1 goes to ground which travels to the upper input to the op. amp. 27 acting as a comparator. Its lower voltage appears from the voltage divider consisting of the resistors R34 and R35. Its output appears across the diode CR3 and the resistor R36. The analog to digital converter for the fault detector centers upon the op. amp. Z8 and includes as well the resistors R37 to R40. Its output appears on the lead L2.

The components finding use in the circuit of FIGS. 2A and 2B appear in the table.

TABLE

| Components Used in FIGS. 2A and 2B | |
|---|---|
| Identification | Component |
| C1, | 2200 pF, 2% |
| C2, C5 | 22 μF |
| C3, C18, C22 | .01 μF |
| C4, C14 | 4.7 μF |
| C6, C7 | 470 pF, 2% |
| C8, C10, C13, C15, C17, C20, C21 | .1 μF |
| C9 | .015 μF |
| C11 | .001 μF |
| C12, C19 | 10 μF |
| C16 | 1 μF |
| CR1 | SE3470-3 |
| CR2 | BAT17 |
| CR3 | IN4148 |
| Q1 | BSS138 |
| Q2 | SFH317F |
| R1 | 2 KΩ |
| R2 | 31.6 KΩ |
| R3, R4 | 150 Ω |
| R5 | 2.7 Ω |
| R6, R20 | 470 KΩ |
| R7 | 100 Ω |
| R8, R11, R14, R22, R32, R35 | 10 KΩ |
| R9 | 82 KΩ |
| R10 | 205 KΩ, 1% |
| R12, R15, R19, R21 | 1 KΩ |
| R13 | 6.04 KΩ, 1% |
| R16, R39 | 22 KΩ |
| R17, R30, R37 | 1 MΩ |
| R18 | 680 Ω |
| R23, R26 | 100 KΩ |
| R24, R25, R27, R28, R31, R36 | 4.7 KΩ |
| R29 | 43 KΩ |
| R33, R34, R38, R40 | 47 KΩ |
| Z1 | NE555 |
| Z2, Z4, Z5, Z7 | TLC2748 |
| Z3 | SL6270 |
| Z6, Z8 | LM393AN |

Accordingly, what is claimed is:

1. A drop detector comprising:
   (A) emitter means for providing an output of em. radiation of a generally specified wavelength;
   (B) pulsing means, coupled to said emitter means, for pulsing on and off at a particular frequency the output of said emitter means;
   (C) receiver means, located on a position to receive the em. radiation from said emitter means, for, upon the receipt of said em. radiation, providing a characteristic electrical signal; and
   (D) detector means, coupled to said receiver means, for detecting the amplitude modulation of the component of said electrical signal having said particular frequency.

2. The drop detector of claim 1 further including band pass filter means, coupled between said receiver means and said detector means, for substantially reducing the amplitude of the components of said electrical signal having a frequency substantially different than said particular frequency.

3. The drop detector of claim 2 further including holding means, coupled to said emitter means and said receiver means, for holding a drip chamber between said emitter means and said receiver means.

4. The drop detector of claim 3 further including buffer means, coupled between said band pass filter means and said detector means, for isolating the current needs of said detector means from said band pass filter means.

5. The drop detector of claim 4 wherein said receiver means includes a phototransistor which, upon the receipt of said em. radiation, undergoes a change in its conductivity from its emitter to its receiver.

6. The drop detector of claim 5 wherein said detector particular frequency is about 10 kHz.

7. The drop detector of claim 6 wherein said detector means detects an amplitude modulation lasting longer than about 10 msec.

8. The drop detector of claim 7 wherein said pulsing means includes timer components for establishing said particular frequency.

9. The drop detector of claim 8 wherein said receiver means further includes biasing means, coupled to said phototransistor, for biasing said phototransistor in its linear range.

10. The drop detector of claim 3 further including gain control means, coupled to said detector means, for maintaining the output of said detector means at a substantially constant level on a time period substantially longer than the time taken by said drops passing between said emitter means and said receiver means.

11. The drop detector of claim 10 further including alarm means, coupled to said gain control means, for providing an indication when said gain control means deviates substantially from said level.

12. A method of detecting drops through an area comprising:

(A) passing through said area a beam of light with a specified wavelength and pulsed at a particular frequency;

(B) receiving at least a portion of said beam after it has passed through said area; and (C) detecting the amplitude modulation of the component of said beam having said particular frequency.

13. The method of claim 12 further including holding a drip chamber in said area.

14. The method of claim 13 wherein the said particular frequency is about 10 kHz.

15. The method of claim 14 wherein the step of detecting the amplitude modulation of the component of said beam having said particular frequency detects an amplitude modulation lasting at least about 10 msc.

16. The method of claim 15 further including maintaining the result of the step of detecting the amplitude modulation of the component of beam having said particular frequency at a substantially constant level.

17. The method of claim 16 further including providing a perceptible indication when the output of the step of detecting the amplitude modulation of the component of said beam having said particular frequency deviates substantially from said level.

* * * * *